(12) United States Patent
Brejl et al.

(10) Patent No.: US 7,590,272 B2
(45) Date of Patent: Sep. 15, 2009

(54) COLON CHARACTERISTIC PATH REGISTRATION

(75) Inventors: Marek Brejl, Eden Praire, MN (US); Samuel W. Peterson, St. Paul, MN (US); Zhujiang Cao, Hopkins, MN (US)

(73) Assignee: Vital Images, Inc., Minnetonka, MN (US)

( * ) Notice: Subject to any disclaimer, the term of this patent is extended or adjusted under 35 U.S.C. 154(b) by 776 days.

(21) Appl. No.: 11/287,161

(22) Filed: Nov. 23, 2005

(65) Prior Publication Data

US 2007/0122016 A1 May 31, 2007

(51) Int. Cl.
*G06K 9/00* (2006.01)
(52) U.S. Cl. .................... 382/128; 382/131; 382/132
(58) Field of Classification Search ............ 382/128, 382/129, 130, 131, 132, 151, 294; 378/4, 378/21, 22, 23, 24, 25, 26, 27, 901; 424/9.1; 600/324, 411, 423
See application file for complete search history.

(56) References Cited

U.S. PATENT DOCUMENTS 7,194,117 B2 * 3/2007 Kaufman et al. ............ 382/128

OTHER PUBLICATIONS

Acar, B., et al., "Medial axis registration of supine and prone CT colonography data", *Proceedings of the 23rd Annual International Conference of the IEEE, Engineering in Medicine and Biology Society*, vol. 3, (2001), 2433-2436.

Nain, D., et al., "Intra-patient Prone to Supine Colon Registration for Synchronized Virtual Colonoscopy", *Proceedings of the 5th International Conference on Medical Image Computing and Computer-Assisted Intervention-Part II*, (2002), 573-580.

Sethian, J. A., *Level Set Methods and Fast Marching Methods*, Evolving Interfaces in Computional Geometry, Fluid Mechanics, Computer Vision, and Materials Science, 2nd Edition, (Series: Cambridge University's Monographs on Applied and Computational Mathematics (No. 3)), (1999), 202 pgs.

\* cited by examiner

*Primary Examiner*—Abolfazl Tabatabai
(74) *Attorney, Agent, or Firm*—Schwegman, Lundberg & Woessner, P.A.

(57) ABSTRACT

This document discusses, among other things, systems and methods for efficiently calculating a registration of multiple characteristic paths of a virtual three-dimensional object. Each path of discrete points is transformed into a piecewise linear parameterization as a function of path length. The paths are smoothed and normalized. The shorter path is partitioned into a number of discrete subintervals. The subintervals are mapped to the longer path using a minimization function that minimizes a cost function resulting in a locally optimal registration. The shorter path is incrementally positioned along the longer path and the minimization is attempted at each position. When the shorter path cannot be shifted any farther, the globally optimal registration is returned.

38 Claims, 7 Drawing Sheets

COLON CHARACTERISTIC PATH REGISTRATION

CROSS-REFERENCE TO RELATED APPLICATION

This patent application is generally related to, but does not claim priority from, Samuel W. Peterson U.S. patent application Ser. No.11/273,938 entitled SURFACE BASED CHARACTERISTIC PATH GENERATION, which was filed on Nov. 15, 2005, and which is incorporated by reference herein in its entirety.

TECHNICAL FIELD

This document relates generally to volumetric imaging of biological or like objects, and particularly, but not by way of limitation to systems and methods to accurately register multiple paths through a three-dimensional virtual object.

BACKGROUND

Early detection of polyps in a colon, which are typically considered precursors to cancer, can greatly increase a patient's chance of survival from colon cancer. Regrettably, many patients are discouraged from obtaining conventional colonoscopies because of the discomfort and invasiveness of the procedure. A "virtual colonoscopy" avoids some of the invasiveness of a conventional colonoscopy and can increase the likelihood of early detection of colon cancer.

In general, a "virtual endoscopy" is performed with a "fly-through" of a computer generated three-dimensional image of an anatomical structure. These methods use computed tomographic (CT) scans and computer imaging software. Three-dimensional modeling has been used in a variety of clinical applications including virtual colonoscopies, virtual bronchoscopies, and virtual angioscopies. In a typical flythrough, a user can move a viewpoint through the reconstructed volumetric object, stopping at certain points to further analyze a suspicious formation on the inner wall of the anatomical model. Virtual colonoscopies have been shown to be effective at detecting small polyps. However, when only one scan is used, extraneous material may be present and cause interference.

Extraneous material such as stool and water can cause both false positives and false negatives. Because the texture and color of a 3D colon model are not represented, the presence of extraneous material makes identification of a polyp-shaped formation more difficult. These types of extraneous materials can obscure a true polyp, causing a false negative. Alternatively, the extraneous material could be mistaken for a polyp, in which case a practitioner may identify a pseudo-polyp and declare a false positive. Using two scans, for example a prone and supine scan, can avoid these problems. Because extraneous materials often shift position between the prone and supine scans, a practitioner can use both scans to detect and differentiate between a true polyp and a pseudo-polyp. The practitioner may also be able to detect polyps that were previously obscured by material in one scan.

During a flythrough, a practitioner may choose to change views from one scan to the other to further analyze a portion of the interior of the virtual colon. After the view change, for the sake of efficiency, it would be ideal to place the practitioner's viewpoint at the same position in the colon. However, typically, the difference in shape and size of the colon between the prone and supine scans can be relatively large. This makes it difficult to manually determine the corresponding position between the scans.

Generally, registration is a method of determining a set of corresponding points between two or more scans. One method of registration is manual registration performed by the practitioner. Typically, the practitioner views the scans together and attempts to pick out characteristic anatomical landmarks to create a baseline correspondence. After this initial orientation, when a practitioner finds a suspicious formation, he can then orient himself in a corresponding scan using the baseline correspondence and page through adjacent images until he is near the same location. This method is tedious, inaccurate, and costly.

SUMMARY

Automated registration of prone and supine colon scans is desirable. One approach would be to first determine similar features in the prone and supine data set. A feature is a local maximum or minimum value in any of the coordinate axes. This approach would use relatively stationary points along the medial axis path of the colon for both data sets as reference points. It then matches these points by stretching and/or shrinking of either the supine or prone path. In one example, this approach relies on the fact that the hepatic and splenic flexures are relatively fixed in location. Therefore, the data points that represent these flexures present features that can be used as reference points in the registration. After correlating the reference points between the supine and prone paths, a linear transformation is used to approximate the points on the paths.

However, this approach may fail when there are insufficient distinguishable features. Also, it usually requires a nearly full prone scan and a nearly full supine scan to allow proper feature matching and the accuracy, although much better than the case where there has been no registration, is still subject to errors that make navigation inefficient.

Because the colon flexes and shifts when a patient changes position, accurate registration is important when performing a virtual colonoscopy. Automated methods that use feature mapping are a natural progression from the manual methods of registration. However, dependence on features is unreliable when the features in an organ can shift and change shape so dramatically.

Another approach uses geometrical or morphological information to register multiple paths. In some approaches, geometric information, such as radius, circumference, or surface curvature related to the shape of the scanned object are used as factors when measuring the relative correspondence between paths. In one approach, a function that uses an average radius about a centerline point is used with dynamic programming to correlate paths. However, to determine the radius around a given point in a path, in some examples, the process must consider volumetric data. In general, processing volumetric data is highly computational. By not requiring the use of volumetric data, the present method achieves higher computational efficiency.

This document describes, among other things, systems and methods for efficiently calculating a registration of multiple characteristic paths of a virtual three-dimensional object. In one example, a first and second path are received as input. Each path of discrete points is transformed into a piecewise linear parameterization as a function of path length. The paths are smoothed and normalized. The shorter path is partitioned into a number of discrete subintervals. As an initial configuration, the shorter path is mapped directly to a portion of the longer path. A cost function is defined, where the cost function contains an error term and a spring term. The error term is a function of a position difference and a slope difference in the x, y, and z planes between corresponding subintervals. The spring term is a function of the ration of lengths between the corresponding subintervals. The subintervals of the shorter path are mapped to corresponding warped intervals along the longer path using a minimization function that minimizes the cost function resulting in a locally optimal registration. The shorter path is incrementally positioned along the longer path and the minimization is attempted at each position. When the shorter path cannot be shifted any farther, the globally optimal registration is returned.

This summary is intended to provide an overview of certain subject matter of the present patent application. It is not intended to provide an exclusive or exhaustive explanation of the invention. The detailed description is included to provide further information about the subject matter of the present patent application.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION

Figure 1:
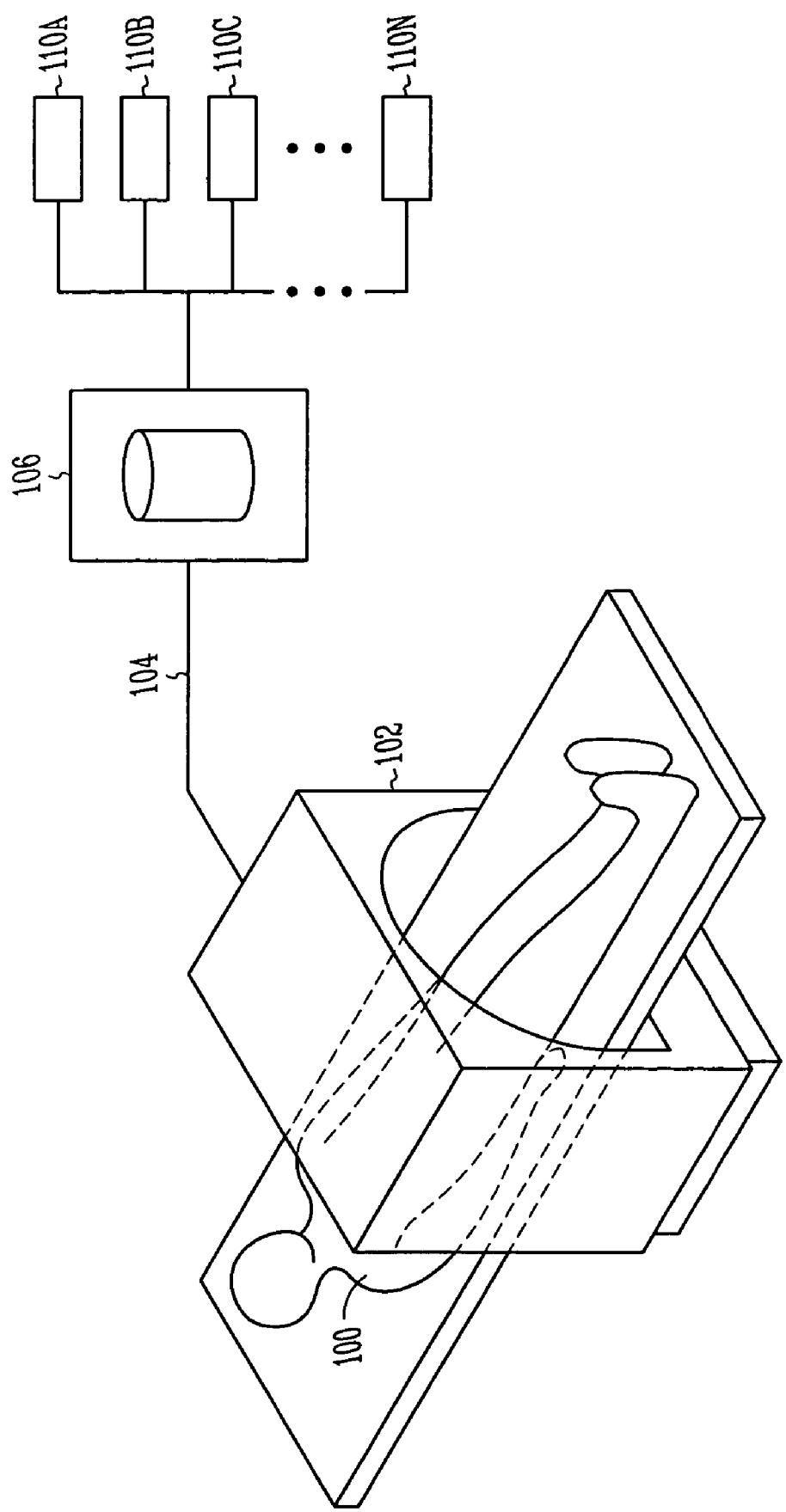
FIG. 1 is a schematic view of a medical scanner, an image storage device, and one or more image processing stations.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the scope of the present invention. The following detailed description is, therefore, not to be taken in a limiting sense, and the scope of the present invention is defined by the appended claims and their equivalents. In this document, the terms "a" or "an" are used, as is common in patent documents, to include one or more than one. In this document, the term "or" is used to refer to a nonexclusive or, unless otherwise indicated. Furthermore, all publications, patents, and patent documents referred to in this document are incorporated by reference herein in their entirety, as though individually incorporated by reference. In the event of inconsistent usages between this documents and those documents so incorporated by reference, the usage in the incorporated reference(s) should be considered supplementary to that of this document; for irreconcilable inconsistencies, the usage in this document controls.

Some portions of the following detailed description are presented in terms of algorithms and symbolic representations of operations on data bits within a computer memory. These algorithmic descriptions and representations are the ways used by those skilled in the data processing arts to most effectively convey the substance of their work to others skilled in the art. An algorithm includes a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like. It should be borne in mind, however, that all of these and similar terms are to be associated with the appropriate physical quantities and are merely convenient labels applied to these quantities. Unless specifically stated otherwise as apparent from the following discussions, terms such as "processing" or "computing" or "calculating" or "determining" or "displaying" or the like, refer to the action and processes of a computer system, or similar computing device, that manipulates and transforms data represented as physical (e.g., electronic) quantities within the computer system's registers and memories into other data similarly represented as physical quantities within the computer system memories or registers or other such information storage, transmission or display devices.

INTRODUCTION

The present inventors have recognized that relying on features or morphological data to register multiple paths will often be inefficient, error-prone, and restrictive. Among other things, this document describes an accurate way to determine a registration of multiple paths without requiring identification of features or reliance on morphological data. Examples of a path include, without limitation, centerline paths or characteristic paths. A characteristic path may not provide complete centricity of the object and, therefore, does not necessarily constitute a centerline. Nevertheless, a characteristic path will typically be sufficiently representative of the object to permit registering a prone scan of the object to a supine scan of the object.

FIG. 1 illustrates an example of a system that may use this characteristic path data. In this example, a patient 100 is scanned by a typical medical imaging scanner 102. Examples of a medical imaging scanner 102 include, without limitation, a CT scanner and a magnetic resonance imaging (MRI) scanner. The scanner 102 is typically connected to a storage system 106, such as by a data pathway 104. The data pathway 104 is typically a local area network (LAN) and the storage system 106 is typically an image server. In this example, the storage system 106 is connected to one or more image processing stations 110A, 110B, 110C, . . . , 110N, by a second data pathway 108, which is typically a LAN.

Figure 2:
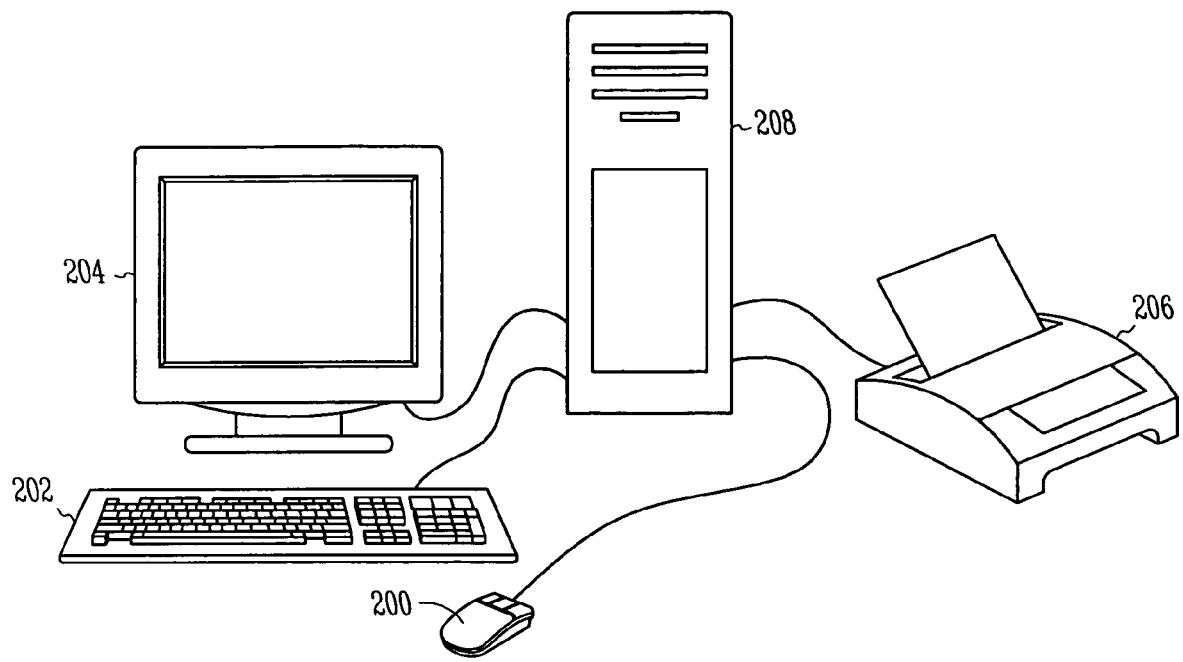
FIG. 2 is a schematic view of an exemplary image processing station.

FIG. 2 illustrates a typical image processing station 110. In this example, the image processing station 110 includes one or more input devices 410, such as a mouse 200 and a keyboard 202, one or more output devices 412, such as a display 204 and a printer 206, and a control unit 208, which may include a processor, a local memory, and additional hardware to control communication between internal and external devices. The image processing station computes a segmentation using the images stored at the storage system 106. The segmentation separates the data representing an object of interest (e.g., a colon) from other nearby objects represented in the data, such as by using image intensity or other information to make such distinctions. A user can use an image processing station 110 to perform a method that includes generating a characteristic path using the segmentation. Multiple characteristic paths can be generated, such as a characteristic path of a colon for a prone patient, and a characteristic path of a colon for a supine patient. Automatic registration between multiple characteristic paths is described below.

Figure 3:
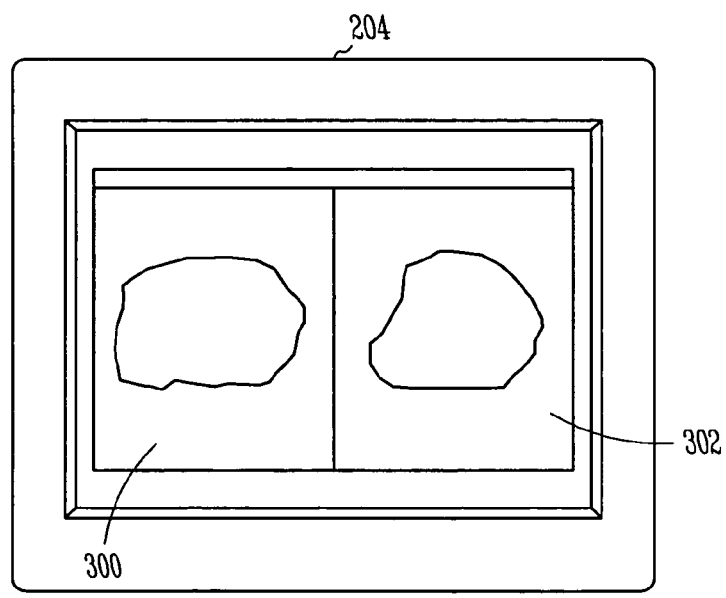
FIG. 3 is a detailed view of a display screen.

FIG. 3 illustrates a monitor 204 displaying two virtual 3D objects concurrently. In this example, each 3D virtual object is a representation of a different scan, such as a supine scan and a prone scan. For example, in a virtual colonoscopy, it is often desirable to take prone and supine scans of the colon, since residual stool content may shift between prone and supine scans making one or the other of the scans more desirable to the diagnostician. However, registering the prone and supine scans is helpful in order to translate between the same location in the prone scan to the same location in the supine scan. The diagnostician may desire to switch between prone and supine scans, such as during virtual flythrough of a colon. Alternatively, during a virtual colon flythrough, as the user maneuvers the point of view through the object's virtual interior in one view 300 (e.g., prone), the other view 302 (e.g., supine) can concurrently track using the provided registration.

EXAMPLES

Figure 4:
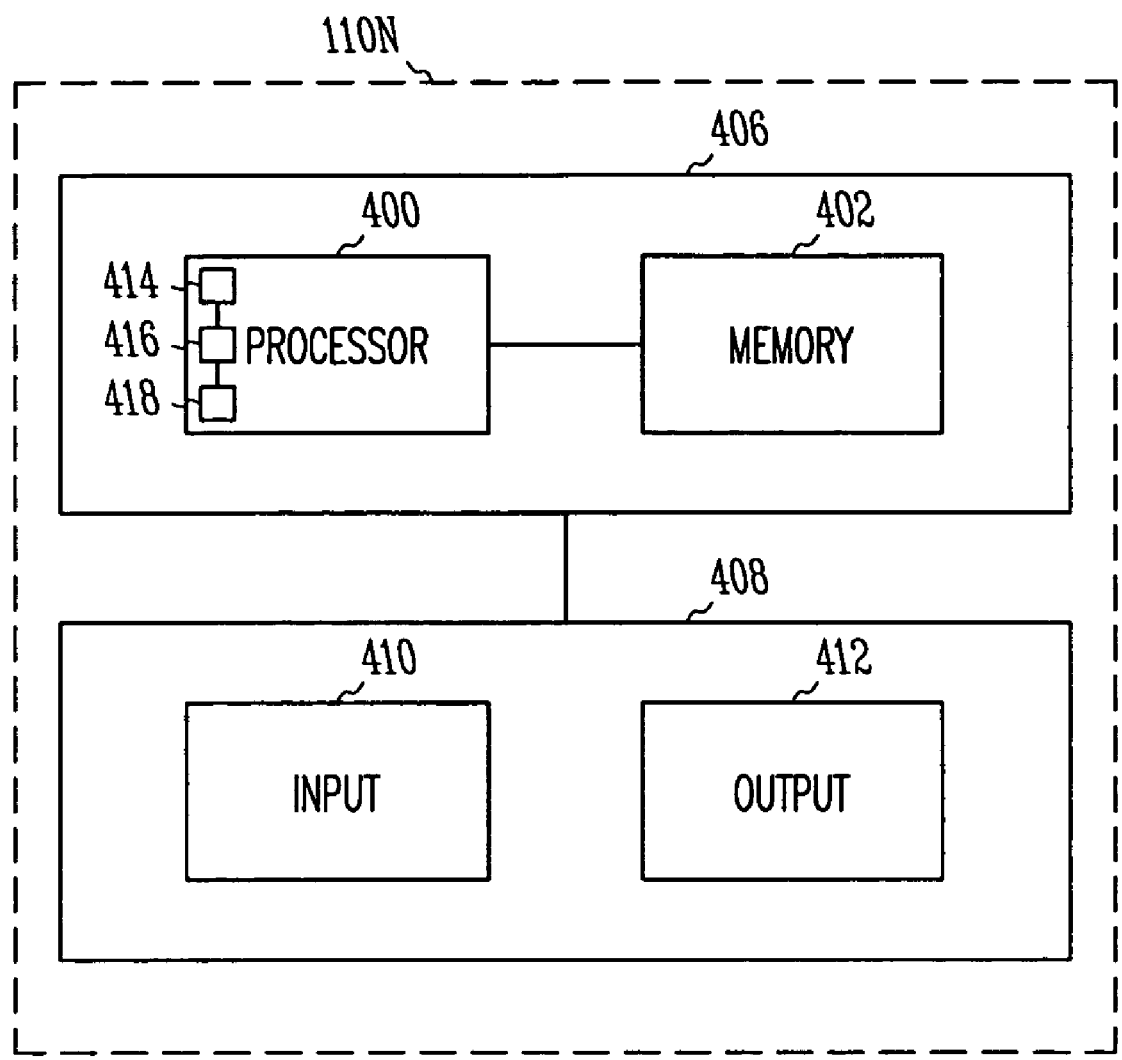
FIG. 4 is a schematic view of a system used to register multiple characteristic paths.

FIG. 4 illustrates portions of a system 110 that is capable of efficient registration of multiple paths independent of features. In this example, a processor 400 is connected to interact with a memory 402. A wide array of possible processor and memory combinations are available. Processors 400 may include commercial units (e.g. Pentium, Motorola 68000 series, PowerPC) or specialized units made for use in specific applications. The memory 402 can include any memory, such as solid-state, magnetic, or optical media.

A user-interface 408 is typically connected to the processor-memory combination 406. This user-interface 408 typically includes an input device 410 an output device 412. The input device 410 can be one or more of a keyboard, a mouse, a touchpad, a microphone, a sensing device, a monitoring device, or any other type of device that allows a computer to receive commands and input data from a user. The output device 412 can include such things as a monitor, a printer, a speaker, or any other type of device that allows a system to represent resultant data to the user.

In one example, a user can input a command with an input device 410 that includes two characteristic paths, typically indicative of a prone scan and a supine scan, respectively. The paths are then used by the processor-memory combination 406 to determine a mapping (i.e., registration) between like points on the multiple paths.

First, the paths are parameterized, smoothed, and partitioned by the Path Preparation module 414. Then, the input parameters for the error minimization function are configured in the Prep Input module 416. Finally, the Registration module 418 determines an optimal solution by minimizing a cost (e.g., energy) function. Then, in one example, the results are displayed on the output device 412 for the user.

Receiving Input

Figure 5:
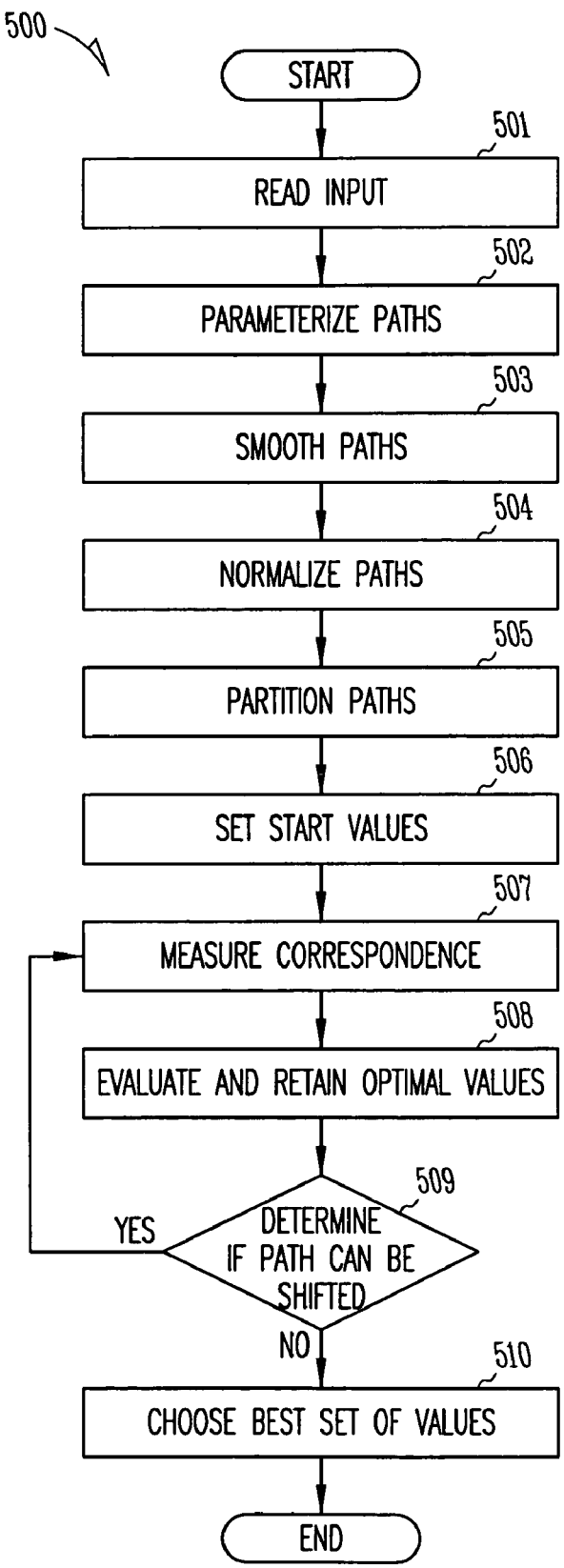
FIG. 5 is a flowchart illustrating generally the process of determining the registration between two characteristic paths.

FIG. 5 is a flowchart illustrating an example of a method 500 for registering two characteristic paths. At 501, the first step is to read the input. In this example, the input will include two characteristic paths, representing a prone and supine path. Each path is described by a sequence of points in 3D space defining a piece-wise linear space curve. A characteristic path can be represented by a sequence of line segments, such that $C=(C_0, C_1, \ldots, C_n)$, where $C_i$ is an (x, y, z) coordinate triplet. Here, the multiple paths can be represented as $C_a=(C_{a0}, C_{a1}, \ldots, C_{an})$ and $C_b=(C_{b0}, C_{b1}, \ldots, C_{bm})$ (e.g., prone and supine characteristic paths) with $\|C_a\| \leq \|C_b\|$ (where $\|C\|$ is the length of C), since one path can be shorter or longer than the other due to stretching or shrinking of a colon as the patient changes from prone to supine position or vice-versa.

In this example, the system 110 is initialized to recognize the paths as representing colon scans, and the only input is the paths. However, in other examples, additional or other parameters may be available to control the operation of the method. In this example, it is assumed that the paths are not smoothed and are generally aligned with each other (e.g., both paths represent the rectum and cecum in the same orientation). If the paths are not generally aligned, then a pre-processing routine can be used to orient the paths to each other. Also in this example, it is assumed that $C_a \tilde{\subseteq} C_b$ (the domain of $C_a$ is approximately a subset of the domain of $C_b$). In other examples, significant portions of $C_a$ may not map onto $C_b$, in which case, techniques that truncate either the head or tail of $C_a$ in an attempt to get a best fit at either the head or the tail of $C_b$ may be used.

Parameterization of the Paths

At 502, the sequence of characteristic path points are parameterized. In this example, each characteristic path is defined by a set of points in 3D space. Parameterization is the process to convert this discrete representation to a representative mathematical function. In this example, given a sequence of signal samples $C=(C_0, C_1, \ldots, C_n)$, the function c(t) (the piecewise linear parameterization of C as a function of characteristic path length) can be defined as the points $$c(0) = C_0$$
$$c(\|C_1 - C_0\|) = C_1$$
$$c(\|C_1 - C_0\| + \|C_2 - C_1\|) = C_2$$
$$\ldots$$
$$\ldots$$
$$c(\|C\|) = C_n, \text{ where } \|C\| = \sum_{i=1}^{n} \|C_i - C_{i-1}\|$$

and linearly interpolating at all values in between. Applying this to the input sequences $C_a$ and $C_b$ results in the parameterized signals $c_a(t)$ and $C_b(t)$.

Smoothing the Paths

At 503, the noise is filtered out and the parameterized signal is smoothed. Generally, smoothed paths are preferred in this example to produce more meaningful slope values, which are used as a factor when determining correspondence during the registration. In certain examples, the signal is smoothed using a Gaussian model defined by the parameter σ. Let δ=min(σ, min(C)), where min(C) denotes the minimum non-zero line segment in C (the input signal points). A one-dimensional discrete Gaussian kernel $G_{\bar{\sigma}}$ is computed, whose standard deviation is given by $\bar{\sigma}=\sigma/\delta$ and whose radius=$\lceil 3\bar{\sigma} \rceil$, as well as a new sequence of signal points $C_\delta$= (c(0), c(δ), c(2δ), c(3δ), . . . , c(‖C‖)). By convolution, a smoothed sequence of signal samples $\tilde{C}=G_{\bar{\sigma}}*C_\delta$, is generated, and thus a smoothed parameterization $\tilde{c}_a(t)$. Applying the smoothing function results in the smoothed signals $\tilde{c}_a(t)$ and $\tilde{c}_b(t)$.

Normalization of the Paths

At 504, the paths are normalized. In this example, the shorter of the two paths, $C_a$, is scaled to a unit measure and defined over the interval [0,1] such that $$\bar{c}_a(t) = \frac{c_a(t \cdot \|C_a\|)}{\|C_a\|}.$$

The longer path, $C_b$, is scaled and defined over the interval $$\left[0, \frac{\|C_b\|}{\|C_a\|}\right]$$

such that $$\bar{c}_b(t) = \frac{c_b(t \cdot \|C_a\|)}{\|C_a\|}.$$

Then, because it is possible for the signals to be slightly offset in position at their start and/or end, the domain of $\bar{c}_b$ is extended to be the entire real line by defining $$\bar{c}_b(t) = \tilde{c}_b(0) \text{ for } t < 0 \text{ and } \bar{c}_b(t) = \tilde{c}_b\left(\frac{\|C_b\|}{\|C_a\|}\right) \text{ for } t > \frac{\|C_b\|}{\|C_a\|}.$$

At this point in the process, $\bar{c}_a(t)$ and $\bar{c}_b(t)$ are smoothed, normalized representations of the paths $C_a$ and $C_b$. In this example, to simplify the notation, $c_a(t)$ will hereafter represent the smoothed, normalized signal $\bar{c}_a(t)$ and $c_b(t)$ will hereafter represent the smoothed signal $\bar{c}_b(t)$.

Partitioning the Paths

At 505, the shorter path is partitioned into a number of samples, which will be individually compared to portions of the longer path in an attempt to find a correspondence. Here, the interval that defines $c_a$ is partitioned into subintervals and can be defined as a sequence of strictly increasing endpoints, the partition P=($t_0$=0, $t_1$, . . . , $t_{k-1}$, $t_k$=1). In this example, an arbitrary number of fifteen discrete subintervals of equal size is used. Other examples may use more or fewer subintervals to provide for a registration. Still other examples may use individual x, y, and z relative maxima and minima along the paths to define the partition. In yet another example, points of maximum and/or minimum curvature along the centerline are used to choose the endpoints of the initial partition. One advantage of using equally sized subintervals is that registration can be performed independent of specific path behaviors or features.

The registration will define a correspondence between the fixed partition P=($t_0$=0, $t_1$, . . . , $t_{k-1}$, $t_k$=1) and the warped partition P'=($t'_0$, $t'_1$, . . . , $t'_k$) ⊂ R. which is a sub-partition of the domain of $c_b$. This correspondence induces a warping of $c_b$ defined by $c_b(W(t))$, where w(t) is a warping function, defined by w(t)=$t'_{i-1}+\phi_i(t-t_{i-1})$, with i chosen such that $t_{i-1} \leq t < t_i$. In this example, φ is the ratio of the length of the warped sub-interval to the original sub-interval.

When determining the correspondence from P to P', to properly reflect the way portions of a colon may stretch or shrink independently from each other, any change to a value of $t'_i$ should not affect the length of any segment that occurs later in the sequence.

Figure 6:
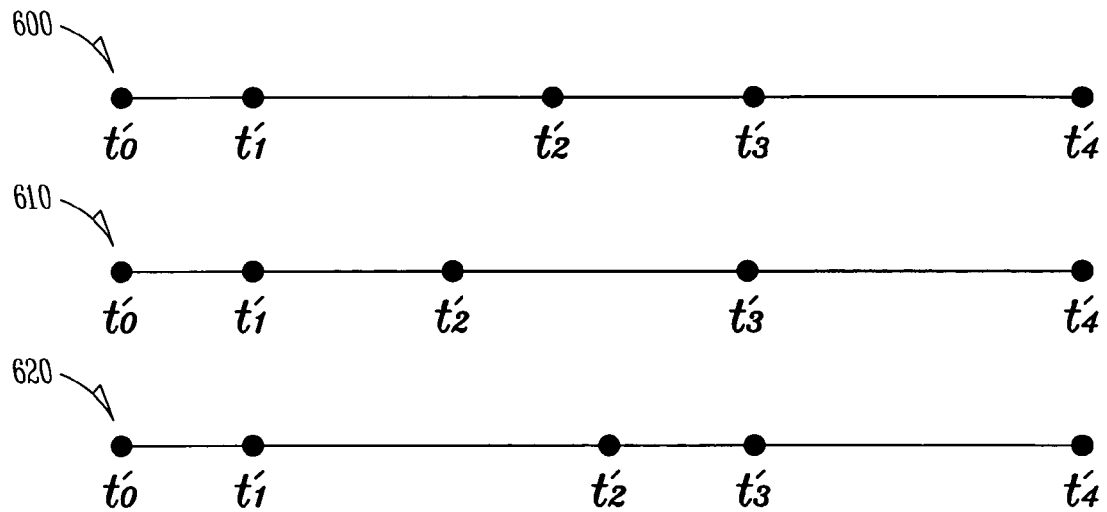
FIG. 6 is a schematic view of several exemplary paths represented by endpoints.

FIG. 6 is an illustration of an initial set of endpoints that define a portion of a path 600, a second set of endpoints 610, where the value $t_2$ has been reduced from its initial value, and a third set of endpoints 620, where the value $t_2$ has been increased from its initial value. In 610, by decreasing $t_2$, the interval $[t_1,t_2]$ has been properly reduced, however, the interval $[t_2,t_3]$ has been improperly increased as a result. Similarly, in 620, by increasing $t_2$, the interval $[t_1,t_2]$ has been properly increased, however, the interval $[t_2,t_3]$ has been improperly decreased. One solution, as used in this example, is to represent the paths by a starting point and a set of length values instead of endpoint values. Thus, let $l'_0=t'_0$, (the starting point of the sub-partition P'), and then $l'_i=t'_i-t'_{i-1}$, i∈{1, 2, . . . k}.

Figure 7:
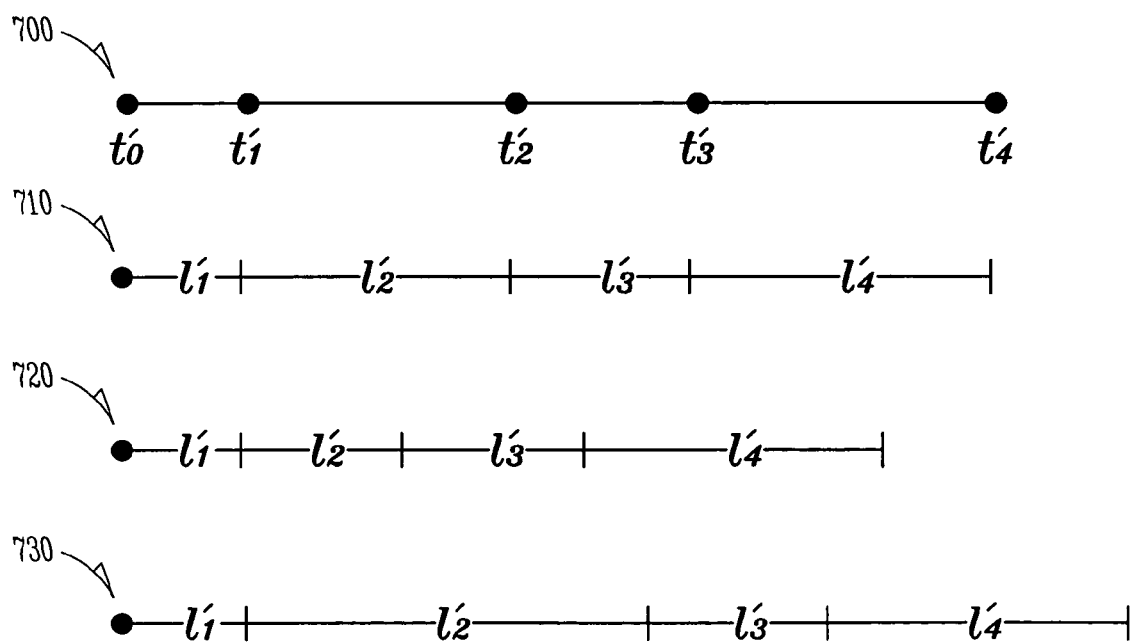
FIG. 7 is a schematic view of several exemplary paths represented by endpoints and lengths.

FIG. 7 is an illustration of a set of endpoints that define a portion of a path 700, the same portion of the path composed of a corresponding initial set of length values 710, an adjusted path 720, where the value $l'_2$ has been reduced from its initial value, and another adjusted path 730, where the value of $l'_2$ has been increased from its initial value. By representing the paths in this manner, increasing or decreasing a length value $l'_i$ will not affect any subsequent length value. However, any change in $l'_i$ will alter the overall length of the path. Using this representation should accurately reflect the behavior of the colon when portions stretch or shrink.

Configure "Energy" Function Variables

At 506, the initial solution for the error minimization function is configured. First, in this example, the assumption is that no stretching or shrinking of the colon has occurred, thus, initially the warped path is mapped directly to the short path such that $l'_1=l_1$, . . . , $l'_k=l_k$. Also, because there is an assumption that there is no shift in the location of the rectum, $l_0=t'_0=t_0=0$.

Find Optimal Correspondence

At 507, an optimal correspondence between the fixed partition P and the warped partition P' is found. In this example, the correspondence is measured using an energy function, E, which represents the cost associated with any error in a proposed correspondence between two subintervals. In certain examples, the energy function has two parts: an error term, e, and a spring term, s, and is computed over all subintervals across the two paths.

The energy function is calculated at each interval along P' such that E(P')=($E_0$(P'), $E_1$(P'), . . . , $E_k$(P')), where $$E_0(P') = \sum_{i=1}^{k} e_i$$

and $$E_j(P') = (1 - t_{j-1}) \cdot s(\phi_j) + \sum_{i=j}^{k} e_i \text{ for } j \leq 1.$$

Here, $$\phi_j = \frac{t'_j - t'_{j-1}}{t_j - t_{j-1}} = \frac{l'_j}{l_j},$$

representing the ratio of the length of the warped sub-interval to that of the original sub-interval. The energy function of the $0^{th}$ location does not include the spring term, $s(\phi_j)$. The spring term characterizes a penalty for any stretching or shrinking of the path and generally helps ensure that the path is well-formed. In the energy function, the term $(1-t_{j-1})$ scales the spring term to the same magnitude as the sum of the error terms.

The spring term is defined as a function of $\phi$, the ratio of the length of the warped sub-interval to the original sub-interval.

$$s(\phi) = \begin{cases} \omega_3 \cdot \left[\csc\left(\max\left(\varepsilon, \frac{\pi\phi}{2}\right)\right) - 1\right] & \phi \leq 1 \\ \omega_3 \cdot \left[\csc\left(\max\left(\varepsilon, \frac{\pi}{2\phi}\right)\right) - 1\right] & \phi < 1 \end{cases}$$

Notice that the function is both continuous and differentiable at all $$\phi \geq \frac{2\varepsilon}{\pi}.$$

Also, the function is reciprocally symmetric such that $$s(\phi) = s\left(\frac{1}{\phi}\right).$$

In other words, the spring energy resulting from shrinking an interval by a factor of $1/\phi$ is equivalent to the spring energy resulting from stretching an interval by a factor of $\phi$.

The error term, e, is composed of two primary components: the difference in x, y, and z positions and the difference in the x, y, and z slopes of each corresponding subinterval. The error term, $e_i$, is thus defined as:

$$e_i = \omega_1(\Delta_{ix} + \Delta_{iy} + \Delta_{iz}) + t_1\max(0, -t'_0) + (1 - t_{k-1})\max\left(0, t'_k - \frac{\|c_b\|}{\|c_a\|}\right) + \omega_2(\Delta'_{ix} + \Delta'_{iy} + \Delta'_{iz})$$

The first term in the error represents the position difference between the values of the two path components. It is computed by integrating the difference between $c_a(t)$ and $c_b(w(t))$ ($c_b$ after the warping) within each subinterval of the partitions with respect to each component:

$$\Delta_{ix} = \int_{t_{i-1}}^{t_i} |c_a(t)_x - c_b(w(t))_x| dt$$

($\Delta_{iy}$ and $\Delta_{iz}$ are similar)

The warping function, $w(t)$, defines a piecewise linear transformation between $c_a(t)$ and $c_b(t)$. As discussed above, the uniform warping between the corresponding intervals $w_i:[t_{i-1}, t_i] \to [t'_{i-1}, t'_i]$ can be defined by $w_i(t) = t'_{i-1} + \phi_i(t - t_{i-1})$. Its derivative is simply $$\frac{d}{dt}(w_i(t)) = \phi_i$$

The second and third terms, $$\max(0, -t'_0) \text{ and } (1 - t_{k-1})\max\left(0, t'_k - \frac{\|c_b\|}{\|c_a\|}\right),$$

are penalty terms for attempted matches that "run off" either end.

The last term measures the differences between the shapes of the two path components by comparing their derivatives after the warp. It is computed by integrating the difference between $d/dt(C_a(t))$ and $d/dt(C_b(w(t)))$ (derivative of $c_b$ after the warping) within each subinterval of the paths with respect to each component:

$$\Delta'_{ix} = \int_{t_{i-1}}^{t_i} \left|\frac{d}{dt}(c_a(t))_x - \frac{d}{dt}(c_b(w(t)))_x\right| dt = \int_{t_{i-1}}^{t_i} |c'_a(t)_x - \phi_i \cdot c'_b(w(t))_x| dt$$

($\Delta'_{iy}$ and $\Delta'_{iz}$ are similar)

The terms in the energy function are weighted using the variables $\omega_1$, $\omega_2$, and $\omega_3$. In this example, these variables are assigned $\omega_1 = 1.0$, $\omega_2 = 0.1$, and $\omega_3 = 0.0004$. In other examples, different weights may be necessary to obtain the best results.

In this example, all three coordinates are used when analyzing the differences in position and slope. Other examples may only examine one or two coordinates in the error function. Also, in this example, each coordinate is weighted equally in the error term. Other examples may weigh coordinates differently based on some preference. Also, this example assumes that a subinterval does not stretch or shrink unevenly. Once the energy function is defined and the initial values are configured, a minimization function is used to determine the local minimum. In this example, the Levenberg-Marquardt technique is used to search for the minimum energy cost in the energy function E, starting at the point $t'_0$ and using the length values $(l'_1 = l_1, \ldots, l'_k = l_k)$. In other examples, other minimization methods could be used, such as the Gauss-Newton method. The result of applying Levenberg-Marquardt is a locally optimal sequence of lengths and an associated set of error values.

Figure 8:
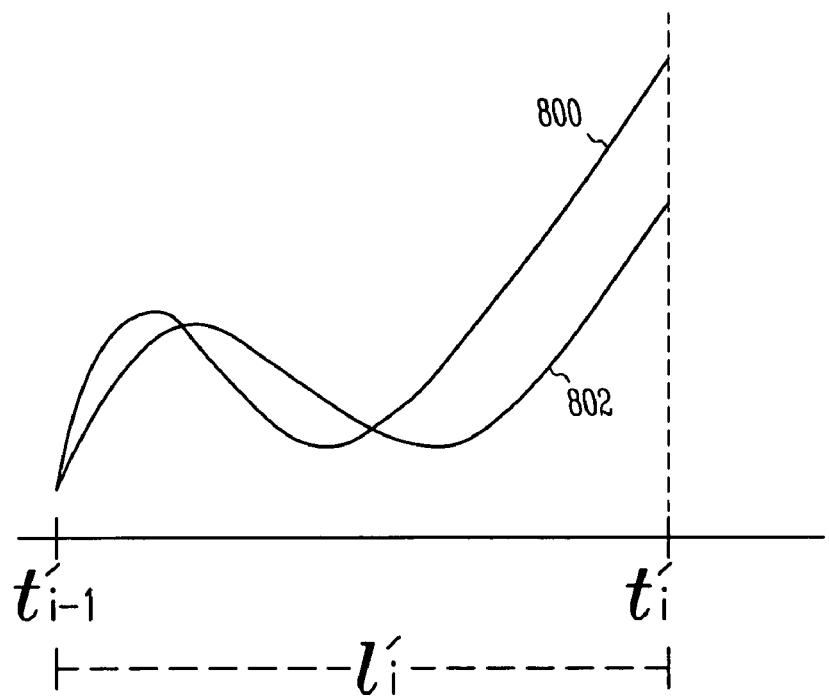
FIG. 8 is a graph of a fixed path and a warped path in an initial position.
Figure 9:
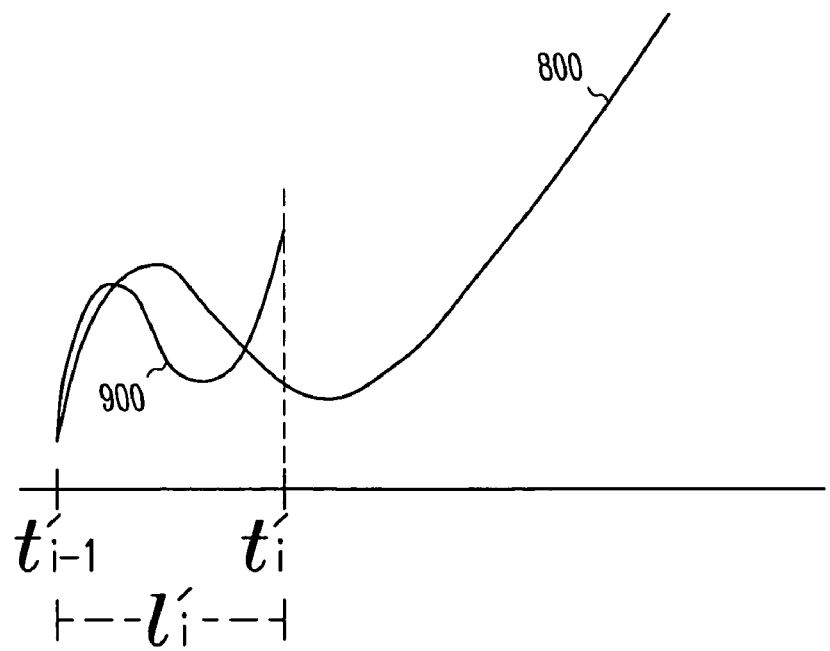
FIG. 9 is a graph of a fixed path and a reduced warped path in a sub-optimal position.
Figure 10:
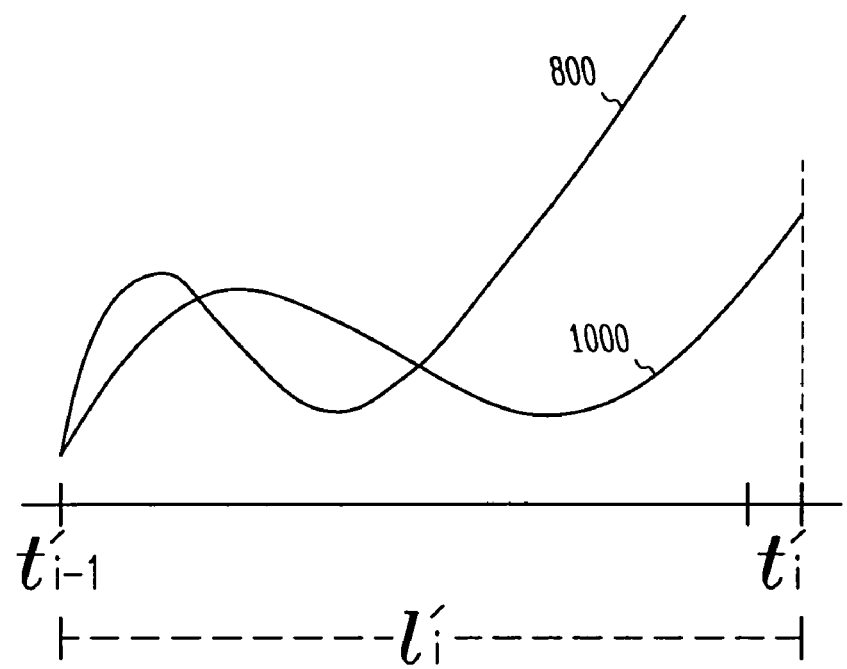
FIG. 10 is a graph of a fixed path and a stretched warped path in a sub-optimal position.
Figure 11:
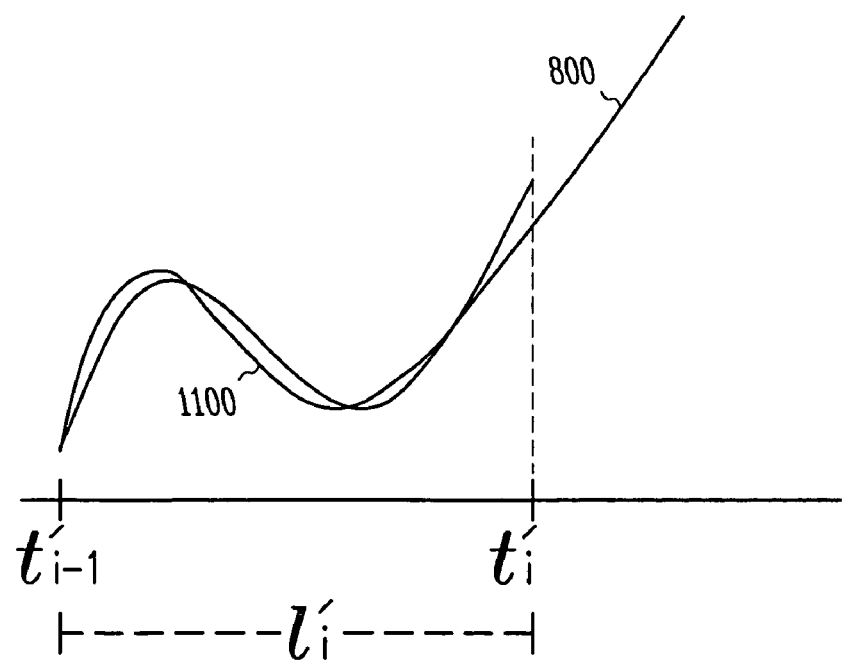
FIG. 11 is a graph of a fixed path and a reduced warped path in an optimal position.

FIG. 8 illustrates an initial alignment of a subinterval of a fixed path 800 and a warped path 802 over the interval $[t'_{i-1}, t'_i]$ with length $l'_i$. The Levenberg-Marquardt technique attempts various solutions that shrink the warped path 900, as illustrated in FIG. 9, and stretch the warped path 1000, as illustrated in FIG. 10, in an effort to find an optimal solution. Referring to FIG. 9, the shrunken warped path 900 is dramatically misaligned with the fixed path 800. In this example, this is not an optimal solution. Referring to FIG. 10, the stretched warped path 1000 is similarly misaligned with the fixed path 800 and does not provide an optimal solution. FIG. 11 illustrates a possible optimal solution, where the warped path 1100 is appropriately aligned with the fixed path 800. In this example, the Levenberg-Marquardt technique attempts to optimize every subinterval concurrently as generally illustrated in FIGS. 8-11.

At 508, the current set of optimal error values is compared to any previously stored set of error values. If it is determined that the current set is more optimal, then it is stored and any previous results are discarded.

When $c_a$ is a subset of $c_b$, then by calculating the correspondence using various seed values for $t'_0$ ranging from 0 to $$\frac{\|c_b\|}{\|c_a\|} - 1,$$

the best overall solution is the most likely match. At 509, if possible, the minimization function is run again with a shifted start value $t'_0$. The shifting can be done using the length of the shorter path as a factor, using the length of the longer path as a factor, using an arbitrary value or percentage, or by other methods. In this example, $c_a$ is shifted along $c_b$ a distance of ¼ the length of $c_a$ by setting $$t'_0 = t'_0 + \frac{\|c_a\|}{4}.$$

If $c_a$ cannot be shifted without extending past the end of $c_b$, then the set of values corresponding to the lowest error is returned as the best registration. Otherwise, the correspondence measurement 507 is performed again with the new start value $t'_0$. If the newly computed error values are better than those stored, then they will replace the stored values. To find the best solution, shifting and recalculation is performed as long as $c_a$ can be shifted along $c_b$.

At 510, the optimal match is returned from the method. In this example, a start point $t'_0$ and a sequence of length values ($l'_1, l'_2, \ldots, l'_k$) are returned representing the best match, or registration, between $c_a$ and $c_b$.

It is to be understood that the above description is intended to be illustrative, and not restrictive. For example, the above-described embodiments (and/or aspects thereof) may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, various features may be grouped together to streamline the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus the following claims are hereby incorporated into the Detailed Description, with each claim standing on its own as a separate embodiment.

What is claimed is:

1. A computer-assisted method of registering multiple paths, the method comprising:
   receiving a first and a second path;
   parameterizing the first and second paths;
   using a computer to measure a correspondence between the first and second paths by:
      minimizing an energy function, wherein the energy function includes an error term and a spring term, wherein the error term is a function of one or more of a position difference, a first derivative, and a second derivative of corresponding discrete subintervals in the first and second paths, and wherein the spring term is a function of the lengths of corresponding discrete subintervals in the first and second paths;
      initializing one or more parameters to the energy function;
      minimizing the energy function to calculate a local optimal correspondence;
      determining if the local optimal correspondence is more optimal than a global optimal correspondence; and
      saving the local optimal correspondence if the local optimal correspondence is more optimal than the global optimal correspondence.

2. The method of claim 1, comprising smoothing the first and second paths.

3. The method of claim 2, wherein the smoothing comprises applying a Gaussian kernel along the first and second paths.

4. The method of claim 1, comprising returning data that represents a correspondence between the first and second paths.

5. The method of claim 4, wherein the data includes a beginning point and a series of adjusted length values.

6. The method of claim 5, wherein the data includes a set of error values that correspond to corresponding length values.

7. The method of claim 1, wherein the parameterizing comprises:
   defining each path as a function with respect to the length of the path;
   normalizing the paths; and
   partitioning the paths.

8. The method of claim 7, wherein the normalizing the paths comprises:
   determining a shorter path and a longer path;
   normalizing the shorter path to a unit value; and
   scaling the longer path with respect to the shorter path.

9. The method of claim 7, wherein the partitioning the paths comprises dividing the shorter path into a set of discrete subintervals, wherein each subinterval has a length value.

10. The method of claim 9, wherein dividing the shorter path, the shorter path is divided into equally sized subintervals.

11. The method of claim 9, wherein dividing the shorter path, the path is divided based on a relative maxima or minima value along the path.

12. The method of claim 9, wherein dividing the shorter path, the shorter path is divided based on a maxima or minima curvature along the path.

13. The method of claim 1, wherein the initializing the one or more parameters comprises:
    defining a start point value, wherein the start point value is a point on the longer path; and
    defining a set of one or more initial length values that map to a partitioned shorter path.

14. The method of claim 1, wherein minimizing the energy function comprises using a minimization function to search for a local minimum in the energy function.

15. The method of claim 14, wherein the minimization function is Levenberg-Marquardt.

16. The method of claim 1, comprising:
    adjusting the one or more parameters to the energy function;
    determining if the minimization can by applied again; and
    if the minimization can be applied again, then applying the energy function to calculate a new local optimal correspondence; and
    storing the new local optimal correspondence if it is more optimal than the global optimal correspondence.

17. The method of claim 1, wherein the adjusting the one or more parameters comprises:
    determining a current start point value, wherein the current start point value is a point on the longer path;
    determining a new start point value, wherein the new start point value is a different point on the longer path than the current start point value; and
    using the new start point value in the one or more parameters to the energy function.

18. The method of claim 17, wherein determining a new start point value comprises adding a portion of a length of the shorter path to the current start point value.

19. The method of claim 1, wherein the function of lengths is a ratio of the lengths.

20. The method of claim 1, comprising using one or more weight values corresponding with the error term or the spring term.

21. A computer-readable medium encoded with computer performable instructions to register multiple paths by:
    receiving a first and a second path;
    parameterizing the first and second paths; and
    measuring a correspondence between the first and second paths by minimizing an energy function, wherein the energy function includes an error term and a spring term, wherein the error term is a function of one or more of a position difference, a first derivative, and a second derivative of corresponding discrete subintervals in the first and second paths, and wherein the spring term is a function of the lengths of corresponding discrete subintervals in the first and second paths;
    initializing a set of one or more parameters to the energy function;
    minimizing the energy function to calculate a local optimal correspondence;
    determining if the local optimal correspondence is a global optimal correspondence; and
    saving the local optimal correspondence if it is more optimal than the global optimal correspondence.

22. The computer-readable medium of claim 21, comprising instructions for smoothing the first and second paths by applying a Gaussian kernel along the paths.

23. The computer-readable medium of claim 21, comprising instructions for returning a data that represents a correspondence, wherein the data includes a beginning point and a series of adjusted length values, and wherein the data includes a set of error values that correspond to each length value.

24. The computer-readable medium of claim 21, wherein the instructions for parameterizing comprises instructions for:
    defining each path as a function with respect to the length of the path;
    normalizing the paths; and
    partitioning the paths.

25. The computer-readable medium of claim 24, wherein the normalizing the paths comprises instructions for:
    determining a shorter path and a longer path;
    normalizing the shorter path to a unit value; and
    scaling the longer path with respect to the shorter path.

26. The computer-readable medium of claim 25, wherein the partitioning the paths comprises instructions for dividing the shorter path into a set of discrete subintervals, wherein each subinterval has a length value.

27. The computer-readable medium of claim 21, wherein the initializing the set of parameters comprises:
    defining a start point value, wherein the start point value is a point on the longer path; and
    defining a set of one or more initial length values that map to a partitioned shorter path.

28. The computer-readable medium of claim 21, wherein minimizing the energy function comprises using a minimization function to search for a local minimum in the energy function.

29. The computer-readable medium of claim 21, comprising:
    adjusting the set of parameters to the energy function;
    determining if the minimization can by applied again; and
    if the minimization can be applied again, then applying the energy function to calculate a new local optimal correspondence; and
    storing the new local optimal correspondence if it is preferable to the global optimal correspondence.

30. The computer-readable medium of claim 29, wherein the adjusting the set of parameters comprises:
    determining a current start point value, wherein the current start point value is a point on the longer path;
    determining a new start point value, wherein the new start point value is a different point on the longer path than the current start point value; and
    using the new start point value in the set of parameters to the energy function.

31. The computer-readable medium of claim 21, comprising instructions for using one or more weight values corresponding with the error term or the spring term.

32. An apparatus for calculating an optimal correspondence between multiple characteristic paths comprising:
    a processor, operable to perform registration of multiple characteristic paths, wherein the registration:
        uses a minimization function to find a minimum cost of an energy function, wherein the energy function includes an error term and a spring term, wherein the error term is a function of one or more of a position difference, a first derivative, and a second derivative of corresponding discrete subintervals in the first and second paths, and wherein the spring term is a function of the lengths of corresponding discrete subintervals in the first and second paths;

initializes a set of one or more parameters to the enemy function;

minimizes the energy function to calculate a local optimal correspondence;

determines if the local optimal correspondence is a global optimal correspondence; and saves the local optimal correspondence if it is more optimal than the global optimal correspondence; and a memory, coupled to the processor, the memory operable for storing data; and a user-interface that permits a user to store and retrieve information from the memory using the processor.

33. The apparatus of claim 32, wherein the processor computes one or more registrations by utilizing the energy function with varying initial parameters and determines an optimal registration from the one or more registrations.

34. The apparatus of claim 32, wherein the processor uses the memory to provide a registration to the user-interface.

35. A computer-assisted method of registering multiple paths, the method comprising:

receiving a first and second path;

parameterizing the first and second paths using a computer; and using a computer to measure a correspondence between the first and second paths by:

minimizing an energy function, wherein the energy function is defined without reference to one or more features that define a hepatic or a splenic flexure;

initializing one or more parameters to the energy function;

minimizing the energy function to calculate a local optimal correspondence;

determining if the local optimal correspondence is more optimal than a global optimal correspondence; and saving the local optimal correspondence if the local optimal correspondence is more optimal than the global optimal correspondence.

36. The method of claim 35, wherein the energy function includes an error term and a spring term, wherein the error term is a function of one or more of a position difference, a first derivative, and a second derivative of corresponding discrete subintervals in the first and second paths, and wherein the spring term is a function of the lengths of corresponding discrete subintervals in the first and second paths.

37. A computer-assisted method of registering multiple paths, the method comprising:

receiving a first and second path;

parameterizing the first and second paths using a computer; and using a computer to measure a correspondence between the first and second paths by:

minimizing an energy function, wherein the energy function is defined without reference to one or more geometric terms describing a virtual volumetric object, wherein the geometric terms include a radius, a circumference, or a surface curvature of the virtual volumetric object;

initializing one or more parameters to the enemy function;

minimizing the enemy function to calculate a local optimal correspondence;

determining if the local optimal correspondence is more optimal than a global optimal correspondence; and saving the local optimal correspondence if the local optimal correspondence is more optimal than the global optimal correspondence.

38. The method of claim 37, wherein the energy function includes an error term and a spring term, wherein the error term is a function of one or more of a position difference, a first derivative, and a second derivative of corresponding discrete subintervals in the first and second paths, and wherein the spring term is a function of the lengths of corresponding discrete subintervals in the first and second paths.

* * * * *

UNITED STATES PATENT AND TRADEMARK OFFICE
CERTIFICATE OF CORRECTION

PATENT NO. : 7,590,272 B2  Page 1 of 1
APPLICATION NO. : 11/287161
DATED : September 15, 2009
INVENTOR(S) : Brejl et al.

It is certified that error appears in the above-identified patent and that said Letters Patent is hereby corrected as shown below:

In column 13, line 27, in Claim 16, delete "can by" and insert -- can be --, therefor.

In column 14, line 42, in Claim 29, delete "can by" and insert -- can be --, therefor.

In column 15, line 6, in Claim 32, delete "enemy" and insert -- energy --, therefor.

In column 16, line 24, in Claim 37, delete "enemy" and insert -- energy --, therefor.

In column 16, line 26, in Claim 37, delete "enemy" and insert -- energy --, therefor.

Signed and Sealed this

Fifth Day of January, 2010

David J. Kappos
*Director of the United States Patent and Trademark Office*

UNITED STATES PATENT AND TRADEMARK OFFICE
CERTIFICATE OF CORRECTION

PATENT NO. : 7,590,272 B2 Page 1 of 1
APPLICATION NO. : 11/287161
DATED : September 15, 2009
INVENTOR(S) : Brejl et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 785 days.

Signed and Sealed this

Twenty-first Day of September, 2010

David J. Kappos
*Director of the United States Patent and Trademark Office*